(12) United States Patent
Oran et al.

(10) Patent No.: US 9,474,839 B2
(45) Date of Patent: Oct. 25, 2016

(54) TRANSARTERIAL HEART ASSIST DEVICE

(76) Inventors: Bulent Oran, Konya (TR); Omer Faruk Oran, Ankara (TR); Elif Oran Avci, Konya (TR)

( * ) Notice: Subject to any disclaimer, the term of this patent is extended or adjusted under 35 U.S.C. 154(b) by 95 days.

(21) Appl. No.: 14/415,737

(22) PCT Filed: Mar. 29, 2012

(86) PCT No.: PCT/TR2012/000055
§ 371 (c)(1),
(2), (4) Date: Jan. 20, 2015

(87) PCT Pub. No.: WO2012/148367
PCT Pub. Date: Nov. 1, 2012

(65) Prior Publication Data
US 2015/0174308 A1 Jun. 25, 2015

(30) Foreign Application Priority Data

Mar. 29, 2012 (TR) .............................. a 2012 00951

(51) Int. Cl.
*A61N 1/362* (2006.01)
*A61M 1/12* (2006.01)
*A61M 1/10* (2006.01)

(52) U.S. Cl.
CPC ............. *A61M 1/122* (2014.02); *A61M 1/101* (2013.01); *A61M 1/127* (2013.01); *A61M 2205/3365* (2013.01); *A61M 2205/505* (2013.01); *A61M 2205/8206* (2013.01); *A61M 2230/04* (2013.01)

(58) Field of Classification Search
USPC .......................................................... 600/16
See application file for complete search history.

(56) References Cited

U.S. PATENT DOCUMENTS

| 2001/0053330 A1* | 12/2001 | Ozaki ................ F04D 13/0666 417/420 |
| 2009/0112312 A1* | 4/2009 | LaRose ................ A61M 1/101 623/3.13 |
| 2009/0149950 A1* | 6/2009 | Wampler .............. A61M 1/101 623/3.13 |
| 2010/0222633 A1 | 9/2010 | Poirier |

FOREIGN PATENT DOCUMENTS

WO  WO2010/042008 A1  4/2010

* cited by examiner

*Primary Examiner* — Nicole F Johnson
*Assistant Examiner* — Nicole F. Lavert
(74) *Attorney, Agent, or Firm* — Gokalp Bayramoglu (57) ABSTRACT

The present invention relates to a Heart Assist Device which comprises a motor, a control unit and an internal battery connected to the motor. The control unit is connected to the motor controlling the motor's operation. The motor of the Heart Assist Device further comprises a rotor without an axial pin running in magnetic bearing. The present disclosure has smaller size and consumes less energy to longer battery lives. The device has high power so that it generates high blood flow. The contact surface is small enough so that it does not cause any harmful effects for blood cells and coagulation systems.

13 Claims, 7 Drawing Sheets

TRANSARTERIAL HEART ASSIST DEVICE

TECHNICAL FIELD

The system is a "transarterial assist device" and its peripheral components that can be installed in aorta and/or pulmonary artery in order to facilitate blood circulation for patients with heart failure.

Device is a support system which utilizes a rotor without a pin running in a magnetic bearing. The device is quite small in size and uses low energy for its operation therefore improving the battery life. The device generates a high volume blood flow because of its efficient and powerful force. The small contact surface helps reducing problems introduced by these type of devices affecting blood elements and coagulation system. The device is dependable and easy to use and successfully push blood through large arteries.

BACKGROUND

Heart assist devices are vital instruments for patients who have contracting hearth muscle problems and who have not responded positively for drug treatments.

In today's world, thousands of patients with coronary artery diseases who have suffered from heart attacks receive cardiac failure treatments. If the patient does not respond to medicine treatment, it becomes necessary to transplant a new heart. It is not easy to find a heart donor. Therefore it is necessary to have heart support devices to prolong patient's life and provide heart support while patient waits for an available heart for a transplant. It is desirable to have a heart support device that is small enough to be used both in adult and infants.

There have been numerous studies for developing heart support devices In order to provide higher life standards for patients who are in waiting lists for heart transplants. Consequently many different support devices have been offered. Jarvic 2000, Lionheart, Coraide, Heartmate II, HeartSaver and Abiocor are examples of heart support devices. Debakey Heart Support Device manufactured by Micormed company with the support of NASA engineers in the U.S.A., is an example of the new generation heart support devices. Because of being small in size and suitable for all ages have made them ideal devices. Since these devices requires less invasive surgical operations, they are better preferred by patients and heart surgeons.

In previous years balloon pumps that have been in placed in aorta were utilized for that purpose. The balloon that is inflated and deflated in synchronous with the heart operation, has aimed to facilitate the blood flow in aorta. Later systems that operate with air pressure have been developed. The pressurized air is provided through out the compressor and the air tank that goes with the patient. One membrane that has been moved forward and backward by means of the pressurized air produces the power that moves the blood forward. Later, systems with electrical motors have been used. Initially these systems were formed by an electrical motor and an attached spiral water turbine. There is one input and one output prosthesis conduit in the system, one end is placed in the heart and the other end is placed in aorta vein, when motor is operated system receives the blood from the heart and pumps it into the aorta.

Systems with pressurized air have been considered inconvenient because of their noisy operations. Systems of electrical motors with great volumes and low efficiency, considered to be inconvenient to install in patients. They were quite energy consuming and also constraining patients' movement capabilities.

BRIEF SUMMARY OF THE INVENTION

The new heart support device would assist blood circulation through an electrical engine without a pin which runs on a magnetic field with helicoidal airfoils. When compared to other similar devices this electrical heart support device has many outstanding features.

The Heart Support Device runs on a magnetic field without a pin, it has a low volume and consequently consumes low energy and results in a longer battery life. Because of its highly efficient operation and the power it generates, it produces high blood flow. Furthermore, the heart support device has smaller contact surface. Therefore problems such as destruction of blood elements due to interaction with machine and blood coagulation are eliminated by this device. The device is small enough that can be placed in large arteries.

DESCRIPTION OF THE REFERENCE NUMERALS

Figure 1:
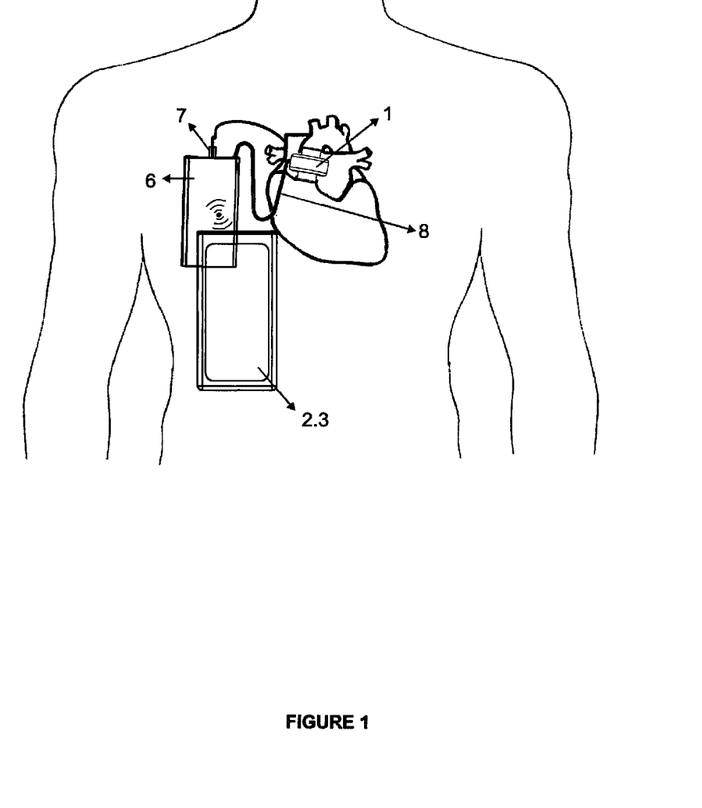
FIG. 1 The heart support system
FIG. 2 The heart support system parts
FIG. 3 The heart support system as installed inside the heart
FIG. 4 Cross section of the heart support system
FIG. 5 The heart support system parts as exploded view
FIG. 6 The heart support system parts as exploded view
FIG. 7 Control Units
Figure 2:
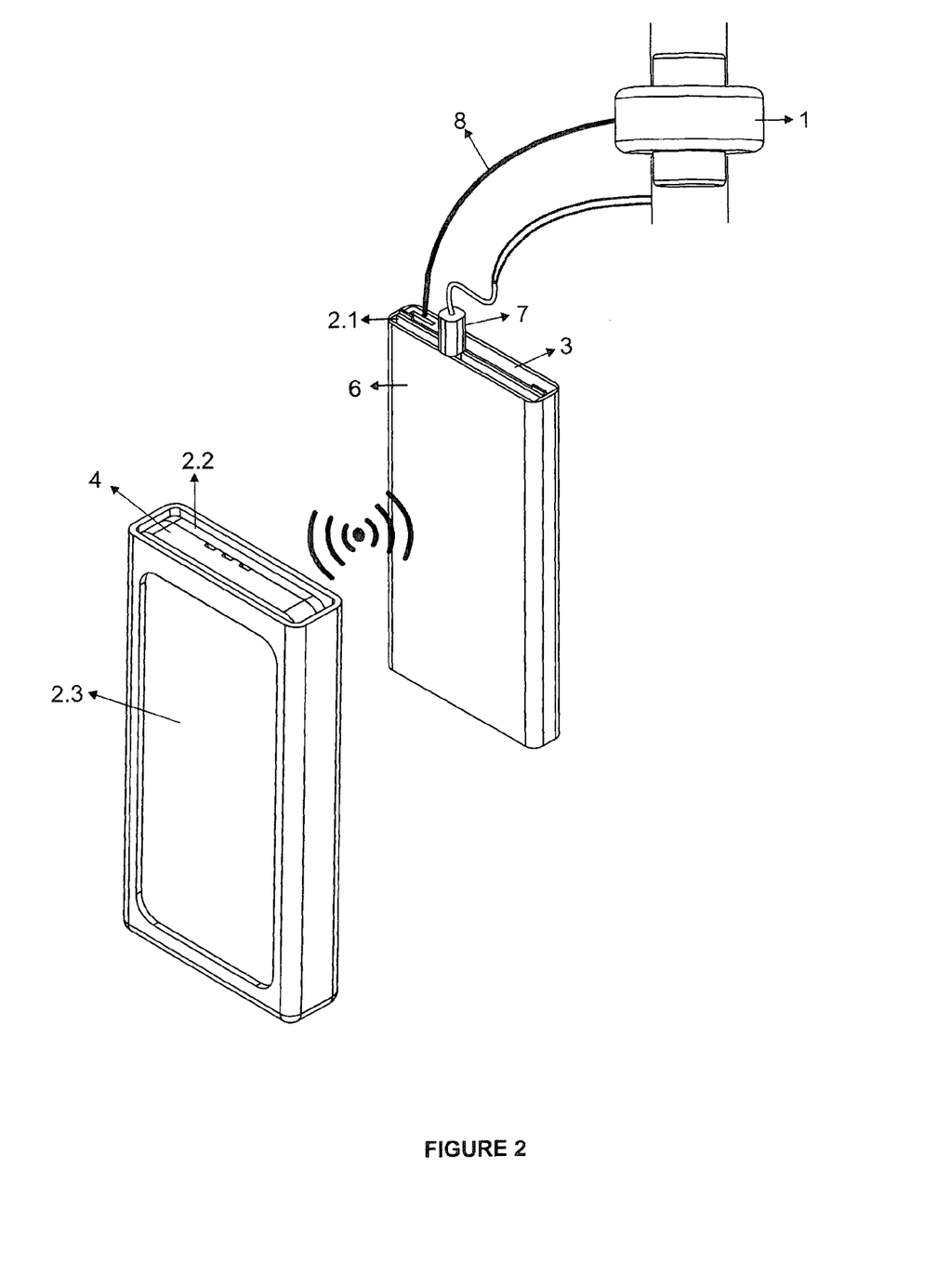
Figure 3:
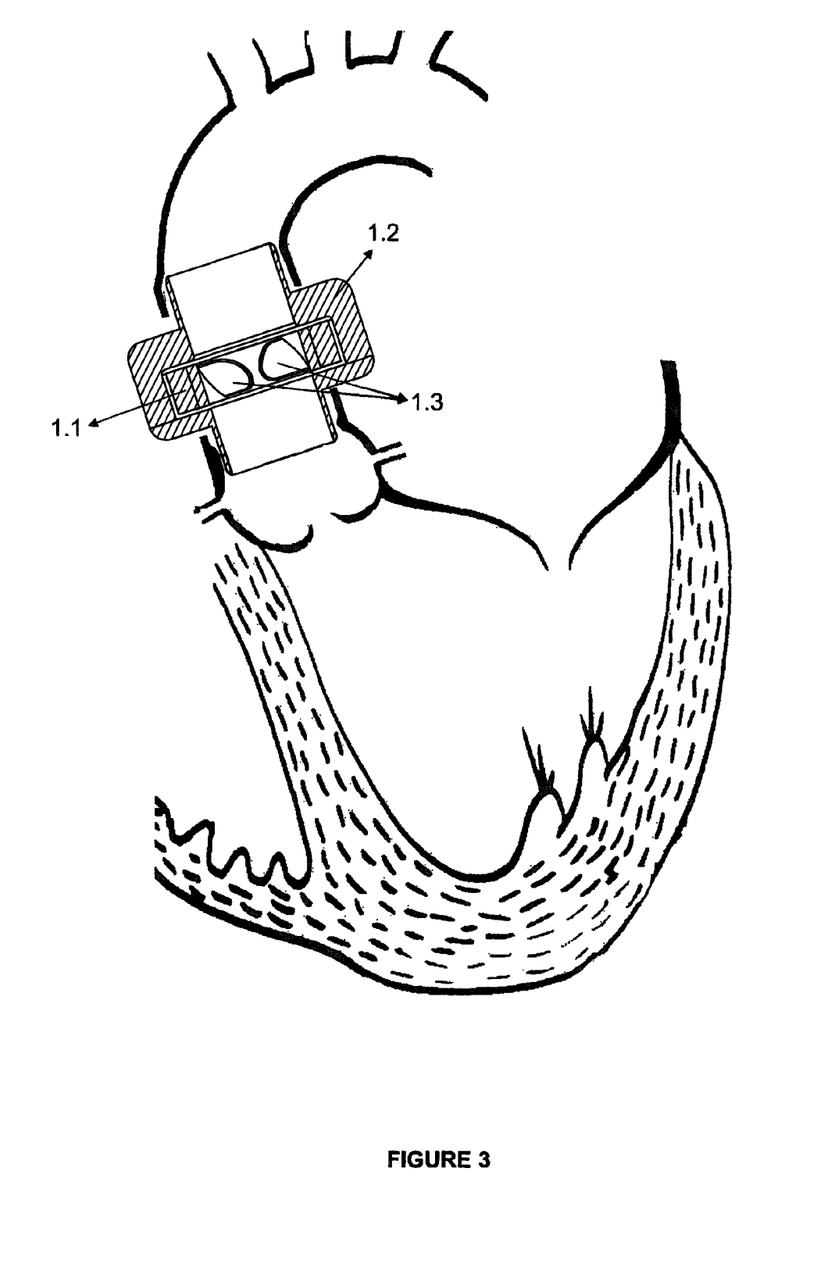
Figure 4:
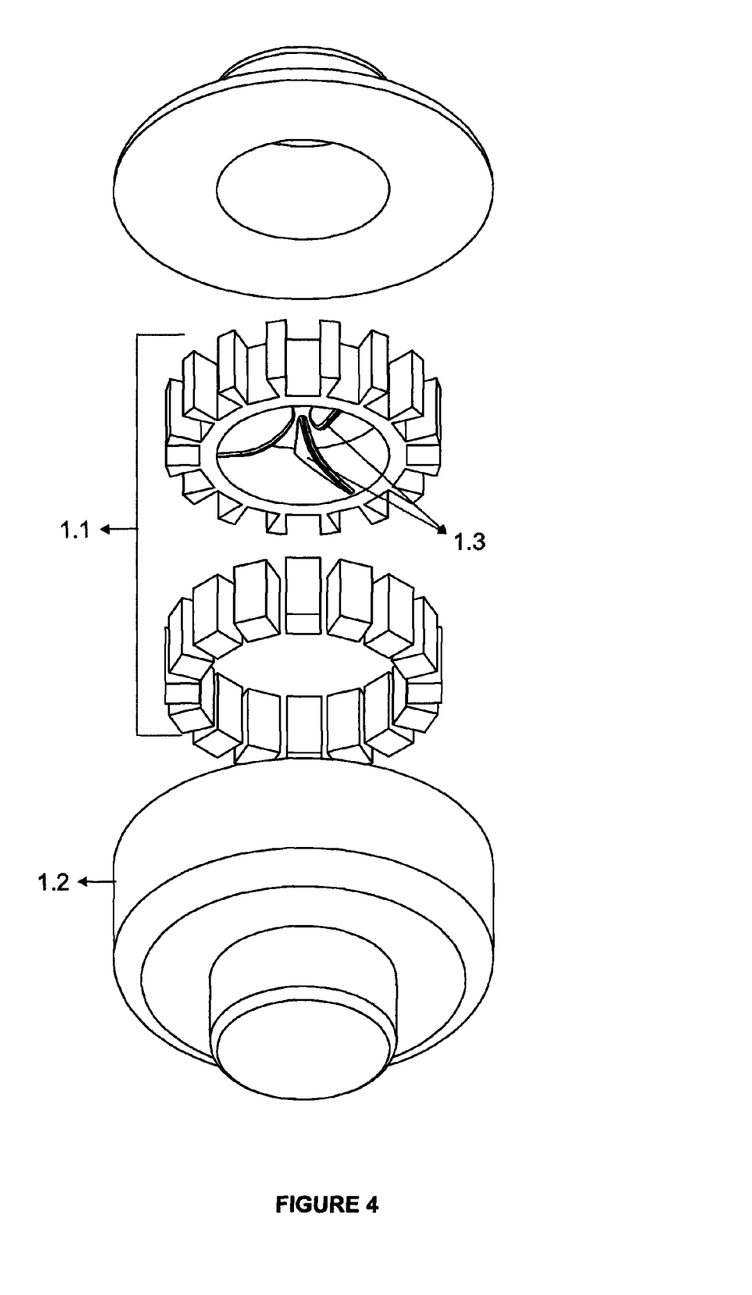
Figure 5:
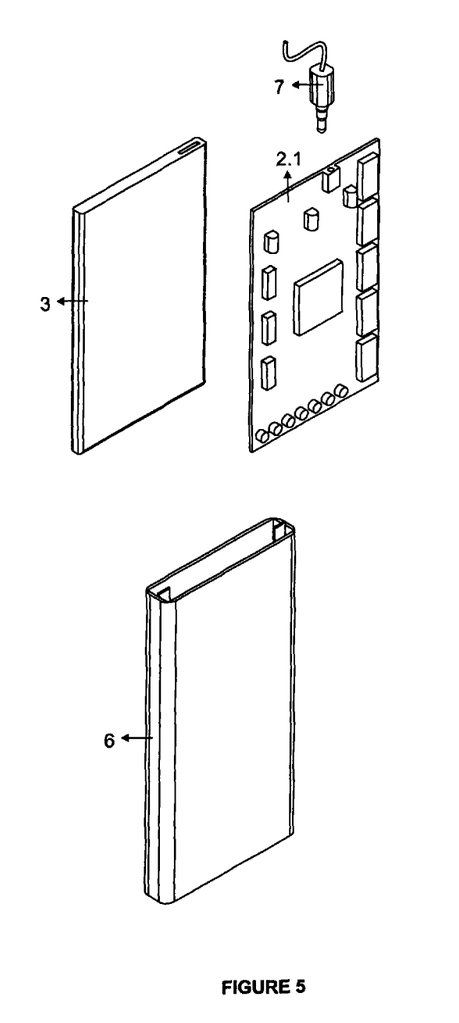
Figure 6:
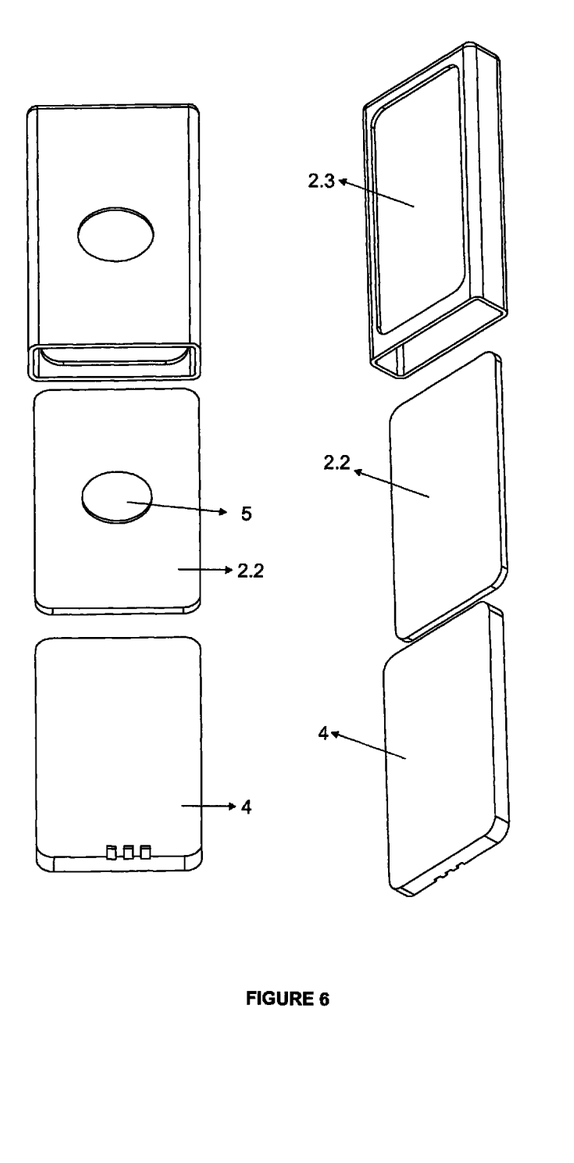
Figure 7:
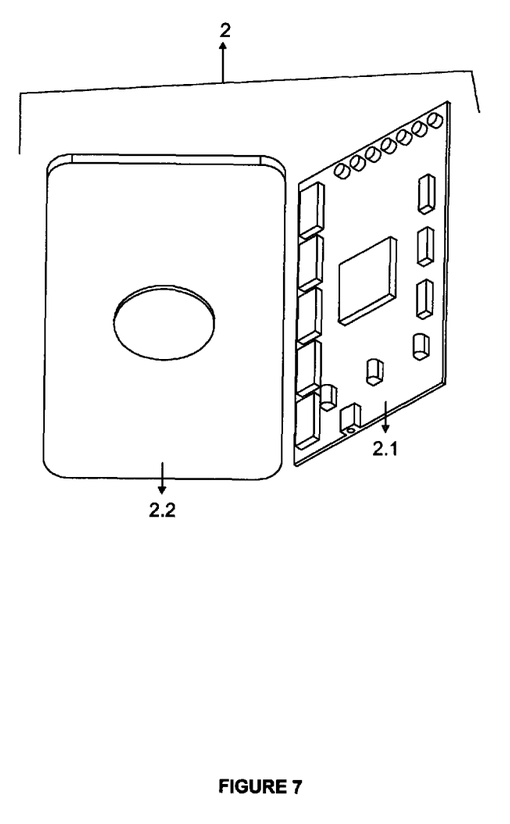

1. Motor
1.1. Rotor
1.2. Stator
1.3. Helicoidal Airfoil (winglet)
2. Control Units
2.1. Internal control unit
2.2. External control unit
2.3. Touch screen
3. Internal Battery
4. External Battery
5. Energy Transfer Apparatus
6. Protective Case
7. ECG wires
8. Electrical power cable

DETAILED DESCRIPTION OF THE INVENTION

The heart support system comprises a motor (1), a control units (2), an internal control units (2.1), an external control units (2.2), an internal battery (3), an external battery (4), an energy transfers apparatus (5), a protective case (6), an ECG wires (7) and an electrical power cable (8). The motor (1); which has a rotor (1.1), a stator (1.2) and at least an airfoil (1.3). Generally composed of two cylindrical parts with the same axis, a stationary (stator) and revolving (rotor).

The heart support system has a rotor (1.1) and a stator (1.2). The stator (1.2) is located at the outer side, the cylindrical rotor which has natural magnet rods, aluminum or copper conductive bars located at the inner side.

The rotor (1.1) revolves in stator freely with the help of the magnetic field (bearing). Since there is no axis pin in the rotor (1.1) the helicoidal airfoils (1.3) are attached at the inner surface and an integrated cylindrical part is formed that rotates together with the rotor (1.1) and takes the blood from backward and pushes it forward.

The motor is made of copper, increasing the efficiency of the motor to more than 95%.

The heart support device has no pin. The rotor runs on a magnetic field with the helicoidal airfoils (1.3) and the copper rotor (1.1) that produces high blood flow. The heart support device is a much smaller device than previous devices. For example this heart support device is much smaller than the Debakey device in size. The heart support device can easily be installed in aorta or pulmonary artery because of its small size. Furthermore when the heart support device is installed in aorta or pulmonary artery that goes to lungs, there is no need to install long artificial veins as required by the previous devices.

Since the heart support device has no pin and the rotor rotates on a magnetic field, the heart support device has less amount of contacting surface with blood. This reduction in contact surface reduces the problems occur regarding the blood cells and coagulation.

A copper rotor (1.1) is made of a metal such as copper, aluminum, titanium, tin or any other appropriate material. The shape of the rotor (1.1) is in the form of an empty cylinder. It runs with electricity. There is at least one helicoidal airfoil (1.3) preferably plurality of helicoidal airfoils attached to the inner surface of the rotor (1.1). When electricity is applied to the rotor (1.1) the rotor (1.1) starts rotating. As the plurality of helicoidal airfoils (1.3) are attached to the inner surface of the rotor (1.1), when the rotor (1.1) rotates, the helicoidal airfoils (1.3) also rotate. This way helicoidal airfoils (1.3) push the blood therefore providing a blood flow.

The heart device is small in size and can easily be installed in the patient's body including newborns and other children.

The heart support device uses small amount of power to efficiently increase the blood flow. As a result, battery life is increased.

Since the heart device is placed in patient's body, consequently such a device with an empty cylindrical rotor (1.1) and helicoidal airfoils (1.3) will provide patients better movement capabilities and comfort.

The heart device has no axial pin at the center of its rotor (1.1). Therefore blood can easily flow through without any obstacle such as a pin or another material.

The control units (2) regulate the operation of the motor. The system has two separate control unit (one of the internal control unit (2.1) and the other external control unit (2.2). The internal control unit (2.1) regulates the operation of the engine (1) and can start and stop the motor (1) just like a natural heart beat with pulsatile flow.

The control unit (2) receives patients ECG signals and works in synchronously with patients ECG signals. This way the internal control unit (2.1) sends a signal to motor so that electricity is applied to motor and motor starts working when heart is in systolic phase. The control unit (2) sends a signal to motor to shut down the electricity so that motor stops working during the heart's diastolic phase. The control unit (2) regulates the operation of the motor so that coroner circulation is not disturbed since coroner blood circulation occurs during diastolic phase. When the rotor stops the blood that comes back trough the helicoidal airfoils (1.3) will feed the coroner arteries.

The motor is placed in aorta due to left ventricle failure could be utilized in right ventricle failures and could also be placed in main pulmonary artery that goes to lungs.

In both right and left heart failure, a motor can be placed in aorta while another motor can be placed in pulmonary artery at the same time. This way a patient will have two motors placed, one in aorta and the other one in pulmonary artery.

The heart support system has two batteries; an external battery (4) and an internal battery (3). The external battery (4) is in the external apparatus and carried by the patient over the shoulder and it can be charged as needed.

There are three pieces of hardware in the external apparatus. The first one featured a lithium-ion rechargeable battery that provides the necessary energy. The second hardware is a power transfer apparatus from external to internal battery (3). Third is the external control unit (2.2) with touch screen. External control unit (2.2) has the ability to remotely control with internal control unit (2.2). Important data constantly updated in real time (state of charge, estimated heart rate and cardiac output) and shows on the touch screen when prompted. Thus, there are an energy transfer apparatus (5) (below), external battery (4) (middle), external control unit (2.2) with touch screen (2.3) (at the top) in the external apparatus.

The internal battery (3) and internal control unit (2.1) are placed together inside a nikel-titanium protective case (6). The protective case (6) can be built using nikel-titanium or any other suitable material. Internal control unit (2) settings, after the main user input, can be changed on the touch screen. The protective case, with the internal battery (3) and the control unit (2) in it, is placed inside the patient's body, outside of the thorax, a place near my heart.

An energy transfer's apparatus (5) transfers the power from outside battery (4) to inside battery (3) by using a wireless technology. The control unit (2) has a microcontroller in it. Control units (2) settings could be changed remotely through a control device.

The motor (1) is a brushless type motor and microprocessors that there is a need for improved brushless motors are exhaustively. The microprocessor carries out this task in the internal control unit (2.1). The microprocessor can control the engine operation in detail: ECG signals are amplified with booster circuit and ADC (Analog to Digital Converter) is read by the microprocessor through. Microprocessor analyzes the signal and systole and diastole at the time the engine stops or starts with different rotation speeds of the rotor.

In order to prevent allergic or toxic effects of copper, iron and aluminum and prevent the corrosion all surfaces that will contact with the blood, the surfaces can be covered by nikel-titanium composition and all electrical installation are isolated from the blood as well.

The invention claimed is:

1. A heart support device configured to be placed in a patient's body comprising:
    a motor, which includes a rotor and a stator; wherein the rotor is in a shape of an empty cylinder; wherein at least one helicoidal airfoil is installed in the inner surface of the empty cylinder of the rotor; and wherein an integrated cylindrical part is formed that rotates together with the rotor and takes the blood from backward and pushes it forward;
    a control unit, which is connected to the motor for controlling the motor's operation; and
    an internal battery connected to the motor;

wherein the inner battery provides a power input for the motor.

2. The heart support device of claim 1, wherein there is no pin in the motor and the rotor rotates on a magnetic field generated by the stator when electricity provided by the inner battery is applied to the stator.

3. The heart support device of claim 1, wherein the rotor is made of copper material.

4. The heart support device of claim 1, wherein the surfaces of the rotor the stator and the at least one helicoidal airfoil are covered by nickel-titanium composition.

5. The heart support device of claim 1, wherein the control unit further comprises an external control unit and an internal control unit which is to ensure the heart runs synchronized with an electrocardiogram (ECG) signals.

6. The heart support device of claim 5, wherein the internal control unit further comprises a microcontroller.

7. The heart support device of claim 1 further comprising an external battery and an energy transfer apparatus.

8. The heart support device of claim 7, wherein the energy transfer apparatus transfer a charge from the external battery to the internal battery via wireless technology.

9. The heart support vice of claim 1, wherein the motor is configured to be placed in aorta.

10. The heart support device of claim 1, wherein the motor is configured to be placed in main pulmonary artery.

11. The heart support device of claim 1, wherein the internal battery and the internal control unit are placed together in a protective case which can be built with nickel-titanium or any other suitable material; wherein the protective case is configured to be placed in the patient's body.

12. The heart support device of claim 5, wherein the control unit further comprises a touch screen which is able to show patient and technical information in real-time.

13. The heart support device of claim 5, wherein a main user can adjust the setting of the control unit.

* * * * *